United States Patent [19]

Föry et al.

[11] Patent Number: 4,854,963
[45] Date of Patent: Aug. 8, 1989

[54] N-HETEROCYCLOSULFONYL-N'-TRIAZINYLUREAS

[75] Inventors: Werner Föry; Willy Meyer, both of Riehen, Switzerland

[73] Assignee: Ciba-Geigy Corporation, Ardsley, N.Y.

[21] Appl. No.: 198,030

[22] Filed: May 24, 1988

Related U.S. Application Data

[62] Division of Ser. No. 872,799, Jun. 11, 1986, Pat. No. 4,759,791.

[30] Foreign Application Priority Data

Jun. 18, 1985 [CH] Switzerland ............... 2566/85
Mar. 5, 1986 [CH] Switzerland ............... 894/86

[51] Int. Cl.$^4$ .................... C07D 411/12; A01N 43/66
[52] U.S. Cl. ......................... 71/91; 71/93; 544/212; 544/207; 544/209; 544/198
[58] Field of Search .............. 71/93, 91; 544/212, 544/207, 209, 198

[56] References Cited

U.S. PATENT DOCUMENTS 4,589,911  5/1986  Ehrenfreund et al. ............. 544/212
4,620,870 11/1986  Pasteris ............................ 544/212
4,634,465  1/1987  Ehrenfreund et al. ............. 544/212

*Primary Examiner*—John M. Ford
*Attorney, Agent, or Firm*—Kevin T. Mansfield; Edward McC. Roberts

[57] ABSTRACT

N-(3,4-Dihydro-2,2-dioxo-1,2-benzoxathiin-8-ylsulfonyl)-N'-pyrimidinylureas, N-(3,4-dihydro-2,2-dioxo-1,2-benzoxathiin-8-yl-sulfonyl)-N'-triazolylureas and N-(3,4-dihydro-2,2-dioxo-1,2-benzoxathiin-8-ylsulfonyl)-N'-triazinylureas of the formula

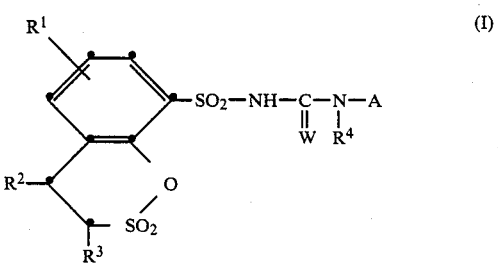

wherein
$R^1$ is hydrogen, halogen, nitro, $C_1$–$C_4$alkyl, $C_1$–$C_4$haloalkyl, $C_1$–$C_4$alkoxy, $C_1$–$C_4$haloalkoxy, $C_1$–$C_4$alkoxycarbonyl, $C_1$–$C_4$alkylthio, $C_1$–$C_4$alkylsulfinyl, $C_1$–$C_4$ alkylsulfonyl or $C_2$–$C_5$alkoxyalkoxy, $R^2$ and $R^3$ are each independently of the other hydrogen or $C_1$–$C_4$ alkyl, $R^4$ is hydrogen, methyl or ethyl,
W is oxygen or sulfur, and
A is a radical

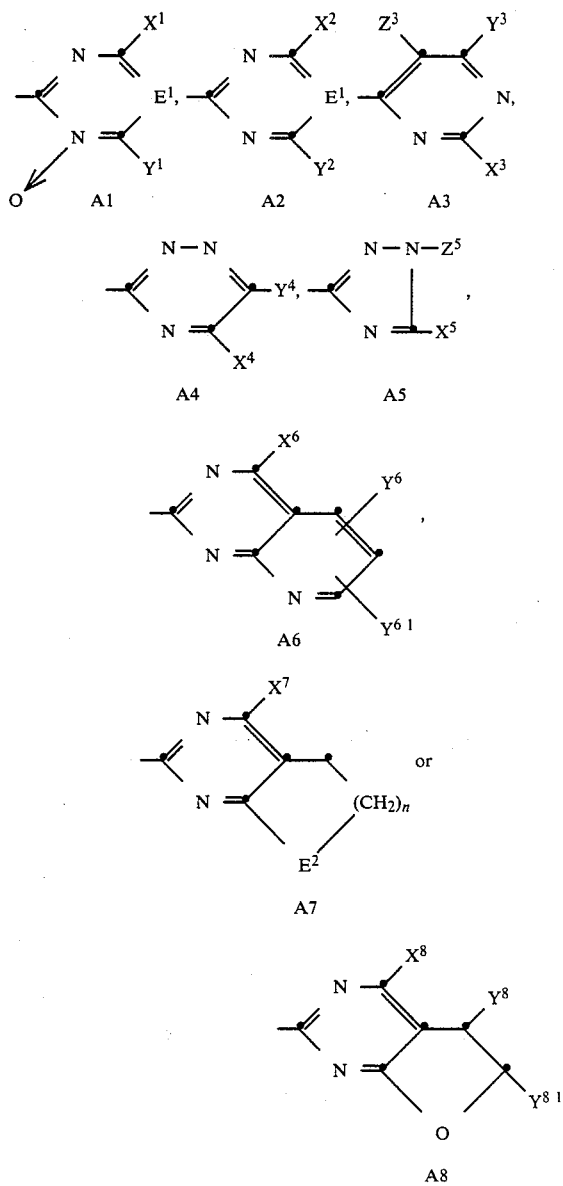

in which formulae the substituents $E^1$, $E^2$, $X^1$, $X^2$, $X^3$, $X^4$, $X^5$, $X^6$, $X^7$, $X^8$, $Y^1$, $Y^2$, $Y^3$, $Y^4$, $Y^6$, $Y^{6\,1}$, $Y^8$, $Y^{8\,1}$, $Z^3$ and $Z^5$ are customary organic radicals, and the salts thereof with amines, alkali metal bases or alkaline earth metal bases or with quaternary ammonium bases have good pre- and postemergence selective herbicidal and growth regulating properties.

15 Claims, No Drawings

N-HETEROCYCLOSULFONYL-N'-TRIAZINYLUREAS

This is a divisional of application Ser. No. 872,799, filed on June 11, 1986, now U.S. Pat. No. 4,759,791.

The present invention relates to novel N-(3,4-dihydro-2,2-dioxo-1,2-benzoxathiin-8-ylsulfonyl)-N'-pyrimidinylureas, N-(3,4-dihydro-2,2-dioxo-1,2-benzoxathiin-8-ylsulfonyl)-N'-triazinylureas and N-(3,4-dihydro-2,2-dioxo-1,2-benzoxathin-8-ylsulfonyl)-N'-triszinylureas with herbicidal and plant growth regulating properties, to the preparation thereof, to compositions containing them as active ingredients, and to methods of using them for controlling weeds, preferably selectively, in crops of useful plants, or for regulating and inhibiting plant growth.

The invention relates to compounds of formula I

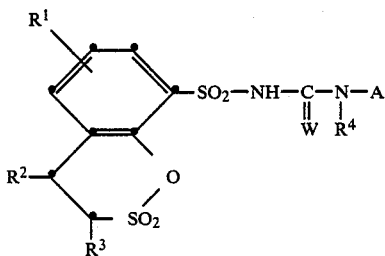

wherein $R^1$ is hydrogen, halogen, nitro, $C_1$-$C_4$alkyl, $C_1$-$C_4$haloalkyl, $C_1$-$C_4$alkoxy, $C_1$-$C_4$haloalkoxy, $C_1$-$C_4$alkoxycarbonyl, $C_1$-$C_4$alkylthio, $C_1$-$C_4$alkylsulfinyl, $C_1$-$C_4$alkylsulfonyl or $C_2$-$C_5$alkoxyalkoxy, $R^2$ and $R^3$ are each independently of the other hydrogen or $C_1$-$C_4$alkyl, $R^4$ is hydrogen, methyl or ethyl, W is oxygen or sulfur, and A is a radical

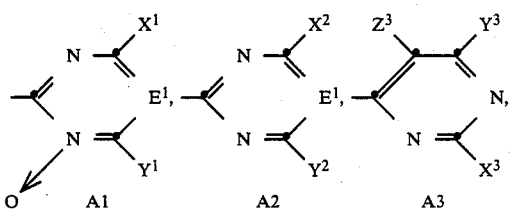

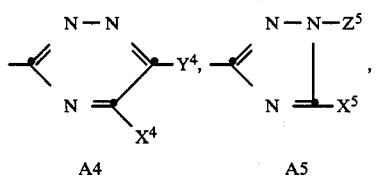

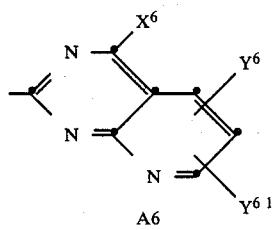

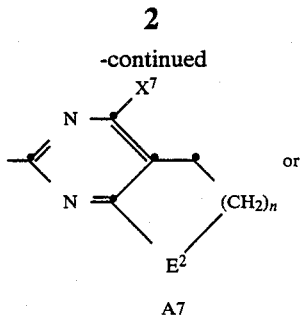

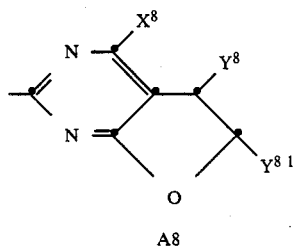

in which formulae $X^1$, $X^2$, $X^3$, $X^4$, $X^5$, $X^6$, $X^7$, $X^8$ and $Y^1$ are each independently halogen, $C_1$-$C_4$haloalkoxy, $C_1$-$C_4$haloalkyl, $C_1$-$C_4$alkoxy, $C_1$-$C_4$alkyl, dimethylamino, methylamino, ethylamino, amino or $C_2$-$C_4$alkoxyalkyl, $E^1$ is nitrogen or the methine bridge, $E^2$ is oxygen or the methylene bridge, $Y^2$ is cyclopropyl, dimethoxymethyl, diethyoxymethyl,

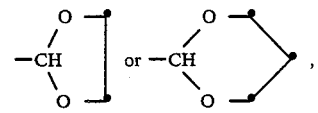

$Y^3$ is methyl, methoxy, ethyl, ethoxy, $C_1$-$C_2$haloalkyl or $C_1$-$C_2$haloalkoxy, $Y^4$ is hydrogen, methoxy, ethoxy, halogen or $C_1$-$C_4$alkyl, $Y^6$ and $Y^{6\,1}$ are each independently of the other hydrogen, $C_1$-$C_4$alkyl, halogen, methoxy or methylthio, $Y^8$ and $Y^{8\,1}$ are each independently of the other hydrogen or methyl, n is 1 or 2, $Z^3$ is hydrogen, methyl, ethyl, methoxy, ethoxy, methoxycarbonyl, ethoxycarbonyl, halogen, cyano, nitro, methylthio, methylsulfinyl or methylsulfonyl, $Z^3$ and $Y^3$ together are a $C_2$-$C_4$alkylene bridge or a $C_2$-$C_4$alkylene bridge which is interrupted by oxygen, and $Z^5$ is methyl or ethyl, or to the salts thereof; with the proviso that $R^3$ is $C_1$-$C_4$alkyl is A is one of the radicals A2 or A5.

Ureas, triazinies and pyrimidines with herbicidal properties are generally known in the art. Sulfonylureas with herbicidal and plant growth regulating properties have recently been described, for example in published European patent applications Nos. 99 339 and 107 979.

In the above definitions, alkyl denotes straight chain or branched alkyl, e.g. methyl, ethyl, n-propyl, isopropyl, or the four butyl isomers.

Alkoxy denotes methoxy, ethoxy, n-propyloxy, isopropyloxy, or the four butyloxy isomers, with methoxy, ethoxy or isopropyloxy being preferred.

Alkylthio is e.g. methylthio, ethylthio, n-propylthio, isopropylthio, or the four butylthio isomers, with methylthio and ethylthio being preferred.

Halogen itself or as moiety of a substituent such as haloalkoxy, haloalkylthio or haloalkyl is fluorine, chlorine and bromine, with fluorine and chlorine being preferred. Haloalkyl itself or as moiety of haloalkoxy or haloalkylthio is normally chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 1,1,2,3,3,3-hexafluoropropyl, with fluoromethyl, chloromethyl, difluoromethyl and trifluoromethyl being preferred.

Alkoxyalkyl is e.g. methoxymethyl, methoxyethyl, methoxypropyl, ethoxyethyl, ethoxymethyl or propyloxymethyl. Alkoxyalkoxy is e.g. methoxymethoxy, methoxyethoxy, methoxypropyloxy, ethoxymethoxy, ethoxyethoxy and propyloxymethoxy. Within the scope of the definition for formula I, alkylene groups are ethylene, propylene, butylene, 1-methylethylene, 1-ethylethylene, 2-methylbutylene, 1-methylbutylene or, if the bridge is interrupted by oxygen, also —CH$_2$—O—CH$_2$— or —CH$_2$—O—CH$_2$—CH$_2$—.

The invention also comprises the salts which the compounds of formula I are able to form with amines, alkali metal bases and alkaline earth metal bases or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine, diethanolamine and 1,4-diazabicyclo[2.2.2]octane being most preferred.

Examples of quaternary ammonium bases are, in general, the cations of haloammonium salts, e.g. the tetramethylammonium cation, the tetraethylammonium cation, the trimethylethylammonium cation, and also the ammonium cation.

Among the compounds of formula I, those compounds are preferred wherein either
(a) W is oxygen or
(b) $R^1$ and $R^2$ are hydrogen and $R^3$ is methyl or
(c) $R^4$ is hydrogen.

A further preferred subgroup of compounds of formula I comprises those compounds wherein W is oxygen and $R^4$ is hydrogen.

Particularly preferred subgroups of compounds of formula I comprise those compounds wherein either
(aa) W is oxygen, $R^4$ is hydrogen and A is the group A1, in which $X^1$ is $C_1$–$C_4$alkyl, or
(bb) W is oxygen, $R^4$ is hydrogen and A is the group A2, in which $Y^2$ is cyclopropyl, or
(cc) W is oxygen, $R^4$ is hydrogen and A is the group A3, in which $Z^3$ is halogen, methyl or ethyl, or
(dd) W is oxygen, $R^4$ is hydrogen and A is the group A3, in which $Z^3$ and $Y^3$ together are a propylene bridge, or
(ee) W is oxygen, $R^4$ is hydrogen and A is the group A5, in which $X^5$ is $C_1$–$C_4$alkoxy and $Z^5$ is methyl or ethyl, or
(ff) W is oxygen, $R^4$ is hydrogen and A is the group A4, in which $X^4$ is $C_1$–$C_4$alkyl or $C_1$–$C_4$alkoxy.

Preferred individual compounds of formula I are:
N-(3,4-dihydro-3-methyl-2,2-dioxo-1,2-benzoxathiin-8-ylsulfonyl)-N'-(4,6-dimethyl-1-oxo-1,3,5-triazin-2-yl)urea,
N-(3,4-dihydro-3-methyl-2,2-dioxo-1,2-benzoxathiin-8-ylsulfonyl)-N'-(2,6-dimethoxy-5-methylpyrimidin-4-yl)urea and
N-(3,4-dihydro-3-methyl-2,2-dioxo-1,2-benzoxathiin-8-ylsulfonyl)-N'-(5,6-dimethyl-1,2,4-triazin-3-yl)urea.

The preparation of the compounds of formula I is generally carried out by the following methods.

In accordance with a first process, the compounds of formula I are obtained by reacting a sulfonamide of formula II

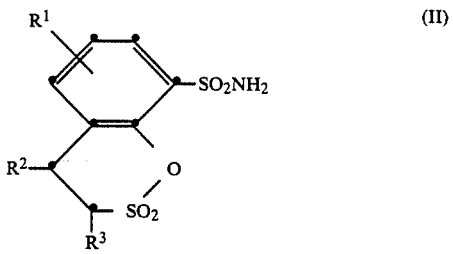

wherin $R^1$, $R^2$ and $R^3$ are as defined for formula I, with a carbamate of formula III

wherein $R^4$, A and W are as defined for formula I and R is phenyl, alkyl or substituted phenyl, in the presence of a base.

In accordance with a second process, the compounds of formula I are obtained by reacting a sulfonylcarbamate of formula IV

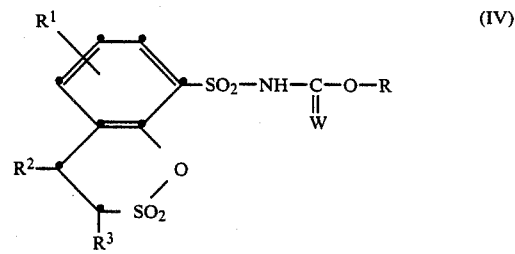

wherein $R^1$, $R^2$, $R^3$ and W are as defined for formula I and R is phenyl, alkyl or substituted phenyl, with an amine of formula V

wherein A and $R^4$ are as defined for formula I.

Finally, the compounds of formula I can also be obtained by reacting a sulfonyl isocyanate of formula VI

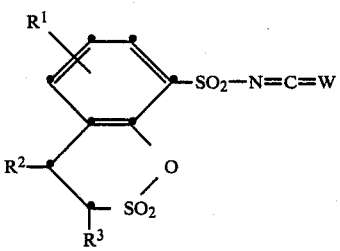

wherein $R^1$, $R^2$, $R^3$ and W are as defined for formula I, with an amine of formula V above.

If desired, the resultant ureas of formula I can be converted into addition salts with amines, alkali metal hydroxides or alkaline earth metal hydroxides or with quaternary ammonium bases. This is accomplished e.g. by reaction with the equimolar amount of base and by evaporating off the solvent.

It is convenient to carry out these reactions for obtaining compounds of formula I in aprotic, inert organic solvents. Examples of such solvents are hydrocarbons such as benzene, toluene, xylene or cyclohexane, carbon tetrachloride, or chlorobenzene; ethers such as diethyl ether, ethylene glycol dimethyl ether, diethylene glycol dimethyl ether, tetrahydrofuran or dioxane; nitriles such as acetonitrile or propionitrile; amides such as dimethylformamide, diethylformamide or N-methylpyrrolidinone. The reaction temperatures are preferably in the range from $-20°$ C. to $+120°$ C. The coupling reactions are normally slightly exothermic and can be carried out at room temperature. To shorten the reaction time or also to initiate the reaction, it is expedient to heat the reaction mixture briefly to boiling point. The reaction times can also be shortened by addition of a few drops of a base as catalyst. Preferred bases are tertiary amines such as trimethylamine, triethylamine, quinuclidine, 1,4-diazabicyclo[2.2.2]octane, 1,5-diazabicyclo[4.3.0]non-5-ene or 1,8-diazabicyclo[5.4.0]undec-7-ene.

However, the bases employed may also be inorganic bases, e.g. hydrides such as sodium hydride or calcium hydride, hydroxides such as sodium hydroxide or potassium hydroxide, carbonates such as sodium carbonate or potassium carbonate, or bicarbonates such as potassium bicarbonate or sodium bicarbonate.

The final products of formula I can be isolated by concentrating and/or evaporating off the solvent and purified by recrystallising or triturating the solid residue in solvents in which they are not readily soluble, e.g. an ether, an aromatic hydrocarbon or a chlorinated hydrocarbon.

The intermediates of formulae II, IV and VI and the preparation thereof are known from published European patent application No. 99 339.

The starting aminopyrimidines, aminotriazoles and aminotriazines of formula V and corresponding carbamates of formula III are either known or they can be prepared by known methods described in the literature.

The compounds of formula I are stable compounds and no precautionary measures are required for handling them.

When used at low rates of application, the compounds of formula I have good selective growth inhibiting and selective herbicidal properties which make them most suitable for use in crops of useful plants, preferably in cereals, rice, cotton, soybeans and maize. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of formula I are effective even when used at very low rates of application.

The compounds of formula I have in addition pronounced growth regulating, especially growth inhibiting, properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whereas vegetative growth is inhibited.

At higher rates of application of compounds of formula I, all tested plants are so severely damaged in their development that they die.

The invention also relates to herbicidal and growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphaic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch" (Handbook of Surfactants), 2nd Edition, C. Hanser Verlag, Munich & Vienna, 1981; M. and J. Ash, "Encyclopedia of Surfactants", Vol. I–III, Chemical Publishing Co., New York, 1980–81.

The agrochemical compositions usually contain 0.1 to 95%, preferably 0.1 to 80%, of a compound of formula I, 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 24%, preferably 88 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% of active ingredient. The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

PREPARATORY EXAMPLES

EXAMPLE P1

N-(3,4-Dihydro-3-methyl-2,2-dioxo-1,2-benzoxathiin-8-ylsulfonyl)-N'-(4-cyclopropyl-6-methylpyrimidin-2-yl)-urea (compound 2.01)

(a) N-(3,4-Dihydro-3-methyl-2,2-dioxo-1,2-benzoxathiin-8-ylsulfonyl)-N'-methylurea A solution of 24.96 g of 3,4-dihydro-3-methyl-2,2-dioxo-1,2-benzoxathiin-8-ylsulfonamide in 120 ml of absolute acetonitrile is cooled to $+8°$ C. After the addition of 6 ml of methyl isocyanate, a solution of 13.4 ml of 1,8-diazabicyclo[5.4.0]undec-7-ene in 15 ml of acetonitrile is added dropwise over 15 minutes at 10° C. The reaction mixture is stirred for a further hour at room temperature. The mixture is subsequently diluted with 180 ml of water. The product is precipitated by the dropwise addition of 48 ml of 2N hydrochloric acid. The precipitate is isolated and dried, affording 26.4 g of N-(3,4-dihydro-3-methyl-2,2-dioxo-1,2-benzoathiin-8-ylsulfonyl)-N'-methylurea with a melting point of 235°–238° C.

(b) 3,4-Dihydro-3-methyl-2,2-dioxo-1,2-benzoxathiin-8-sulfonyl isocyanate 14.3 g of N-(3,4-dihydro-3-methyl-2,2-dioxo-1,2-benzoxathiin-8-ylsulfonyl)-N'-methylurea are suspended in 143 ml of dry dichlorobenzene. 9.5 g of phosgene are introduced into the mixture over 75 minutes at 140° C. Dry nitrogen is subsequently blown through the reaction mixture for 20 minutes. With the exclusion of moisture, the solution is concentrated by evaporation at 90° C./20 mbar, affording 15.1 g of 3,4-dihydro-3-methyl-2,2-dioxo-1,2-benzoxathiin-8-ylsulfonyl isocyanate in the form of an oil which is dissolved in warm absolute dioxane and, without further storage, is reacted in the subsequent step (c).

(c)

66.5 ml of a 10.78% solution of 3,4-dihydro-3-methyl-2,2-dioxo-1,2-benzoxathiin-8-ylsulfonyl isocyanate in dioxane is added dropwise over 5 minutes at room temperature to a mixture of 3.72 g of 2-amino-4-cyclopropyl-6-methylpyrimidine in 100 ml of absolute dioxane. The mixture is stirred for a further 18 hours and then concentrated by evaporation. The residue is crystallised by trituration with a 1:2 mixture of ethyl acetate and petroleum, affording 11.2 g of N-(3,4-dihydro-3-methyl-2,2-dioxo-1,2-benzoxathiin-8-ylsulfonyl)-N'-(4-cyclopropyl-6-methylpyrimidin-2-yl)urea with a melting point of 216°–217° C.

The compounds of formula I listed in the following Tables are prepared in analogous manner.

TABLE 1

| Comp. No. | $E^1$ | $X^1$ | $Y^1$ | m.p. [°C.] |
|---|---|---|---|---|
| 1.01 | CH | $CH_3$ | $OCH_3$ | 148–150 |
| 1.02 | CH | $CH_3$ | $CH_3$ | 181–182 |
| 1.03 | N | $CH_3$ | $CH_3$ | 162–163 |
| 1.04 | CH | $CH_3$ | $OC_2H_5$ | |
| 1.05 | CH | $OCH_3$ | $OCH_3$ | |
| 1.06 | CH | $N(CH_3)_2$ | $OCH_3$ | |

TABLE 2

| Comp. No. | $E^1$ | $X^2$ | $Y^2$ | m.p. [°C.] |
|---|---|---|---|---|
| 2.01 | CH | $CH_3$ | cyclopropyl | 216–217 |
| 2.02 | N | $OCH_3$ | cyclopropyl | 186–187 |
| 2.03 | CH | $OCH_3$ | cyclopropyl | |
| 2.04 | N | $CH_3$ | cyclopropyl | |

TABLE 3

| Comp. No. | $X^3$ | $Y^3$ | $Z^3$ | m.p. [°C.] |
|---|---|---|---|---|
| 3.01 | $OCH_3$ | $OCH_3$ | Cl | 227–228 |
| 3.02 | $CH_3$ | $OCH_3$ | Cl | 221–223 |
| 3.03 | $OCH_3$ | $CH_3$ | Br | 212–213 |
| 3.04 | $OCH_3$ | $-CH_2-CH_2-CH_2-$ | | 221–222 |
| 3.05 | $OCH_3$ | $OCH_3$ | $CH_3$ | 215–216 |
| 3.06 | $OCH_3$ | $OCH_3$ | F | |

TABLE 4
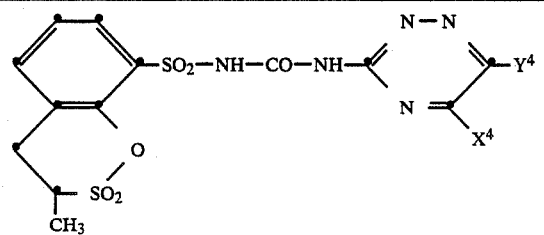
| Comp. No. | X⁴ | Y⁴ | m.p. [°C.] |
|---|---|---|---|
| 4.01 | CH₃ | CH₃ | 161–162 |
| 4.02 | CH₃ | H | |
| 4.03 | OCH₃ | H | |
| 4.04 | OCH₃ | OCH₃ | |
TABLE 5
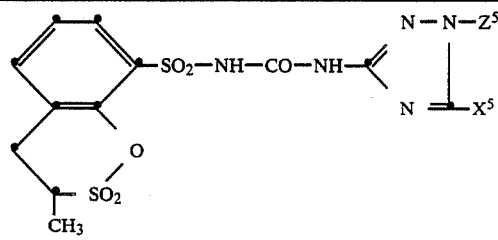
| Comp. No. | X⁵ | Z⁵ | m.p. [°C.] |
|---|---|---|---|
| 5.01 | OCH₃ | CH₃ | 198 |
| 5.02 | CH₃ | CH₃ | |
TABLE 6
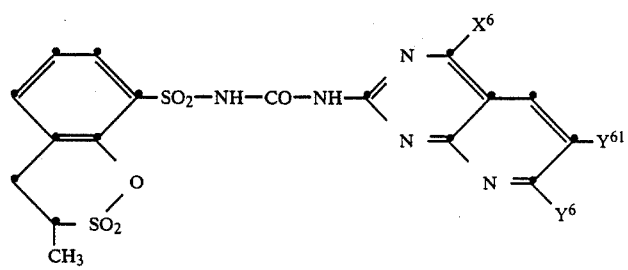
| Comp. No. | X⁶ | Y⁶ | Y⁶¹ |
|---|---|---|---|
| 6.01 | OCH₃ | CH₃ | H |
| 6.02 | OCH₃ | H | CH₃ |
| 6.03 | CH₃ | CH₃ | H |
TABLE 7
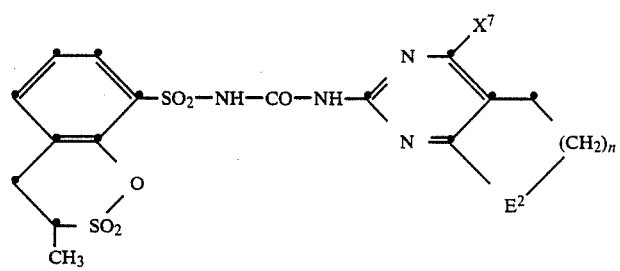
| Comp. No. | E² | n | X⁷ |
|---|---|---|---|
| 7.01 | O | 1 | CH₃ |
| 7.02 | O | 1 | OCH₃ |
| 7.03 | CH₂ | 1 | OCH₃ |
| 7.04 | O | 2 | OCH₃ |
| 7.05 | CH₂ | 2 | OCH₃ |
| 7.06 | CH₂ | 1 | CH₃ |

TABLE 8

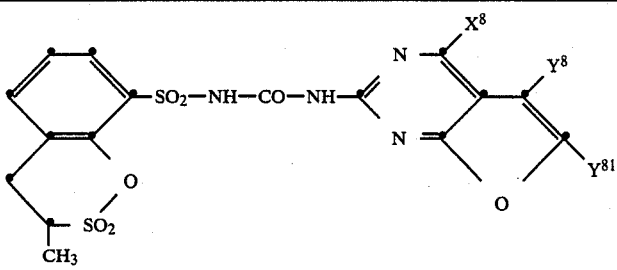

| Comp. No. | $X^8$ | $Y^8$ | $Y^{81}$ |
|---|---|---|---|
| 8.01 | $CH_3$ | H | $CH_3$ |
| 8.02 | $OCH_3$ | H | $CH_3$ |
| 8.03 | $OCH_3$ | H | H |
| 8.04 | $CH_3$ | H | $CH_3$ |
| 8.05 | $OCH_3$ | $CH_3$ | $CH_3$ |

Formulation Examples

Example F1

Formulation Examples for compounds of formula I (percentages are by weight)

| (a) Wettable powders | (a) | (b) | (c) |
|---|---|---|---|
| compound of formula I | 20% | 50% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| compound of formula I | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of formula I | 0.1% | 1% |
| talcum | 99.9% | — |
| kaolin | — | 99% |

Dusts which are ready for use are obtained by mixing the active ingredient with the carrier, and grinding the mixture in a suitable mill.

| (d) Extruder granulate | (a) | (b) |
|---|---|---|
| compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | | |
|---|---|---|
| compound of formula I | 3% | |
| polyethylene glycol (mol. wt. 200) | 3% | |
| kaolin | 94% | |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | | |
|---|---|---|
| compound of formula I | 5% | |
| isopropylamine | 1% | |
| octylphenol polyethylene glycol ether (78 moles of ethylene oxide) | 3% | |
| water | 91% | |

Biological Examples

EXAMPLE B1

Preemergence herbicidal action

Plastic pots are filled with expanded vermiculite (density: 0.135 g/cm$^3$, water-absorbing capacity: 0.565 l/l). After the non-adsorptive vermiculite has been saturated with an aqueous emulsion in deionised water which contains the test compound in a concentration of 70.8 ppm, seeds of the following plants ae sown on the surface: *Nasturtium officinalis, Agrostis tenuis, Stellaria media* and *Digitaria sanguinalis*. The pots are then kept in a climatic chamber at 20° C., an illumination of about 20 klux and a relative humidity of 70%. During the germinating phase of 4 to 5 days, the pots are covered with lightpermeable material and watered with deionised water to increase the local humidity. After the 5th day, 0.5% of a commercial liquid fertilser (Greenzit®, ex Ciba-Geigy) is added to the water. The test is evaluated 12 days after sowing and the action on the plants is assessed according to the following rating:

1: plants have not emerged or are totally withered
2-3: very pronounced action
4-6: medium action
7-8: weak action
9: no action (as untreated controls).

Preemerence action:
Concentration of the test compound emulsion: 70.8 ppm

| Test plant Compound No. | Nasturtium | Stellaria | Agrostis | Digitaria |
|---|---|---|---|---|
| 1.01 | 3 | 4 | 4 | 3 |
| 1.02 | 4 | 3 | 4 | 3 |
| 1.03 | 1 | 1 | 1 | 1 |
| 2.01 | 4 | 4 | 4 | 4 |
| 2.02 | 4 | 4 | 4 | 4 |
| 3.01 | 4 | 4 | 4 | 4 |
| 3.02 | 4 | 3 | 3 | 3 |
| 3.03 | 4 | 4 | 4 | 4 |
| 3.04 | 4 | 3 | 4 | 3 |
| 3.05 | 2 | 1 | 2 | 1 |
| 4.01 | 1 | 1 | 1 | 1 |
| 5.01 | 3 | 3 | 3 | 3 |

EXAMPLE B2

Growth inhibition of tropical leguminous cover crops

The test plants (*Centrosema plumieri* and *Centrosema pubescens*) are reared until fully grown and then cut back to a height of 60 cm. The plants are sprayed 7 days later with an aqueous emulsion of the test compound. The test plants are kept at 70% relative humidity and 600 L lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

EXAMPLE B3

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of formula I until thoroughly wetted. The concentration corresponds to up to 100 g a.i. per hectare. Evaluation is made about 5 weeks after application. Compared with untreated controls, the compounds of formula I markedly increase the number and weight of the harvested siliquae on the leading shoot.

EXAMPLE B4

Growth inhibition of cereals

Summer barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of the formula I. The concentration corresponds to up to 100 g of active ingredient per hectare. Evaluation of the growth of the cereals is made 21 days after application. A comparison with untreated controls shows that the new growth of cereal plants treated with compounds of formula I is reduced (60-90% of the controls) and that the diameter of the stalks has in some cases increased.

EXAMPLE B5

Growth inhibition of grasses

Seeds of the grasses *Lolium perenne, Poa pratenis, Festuca ovina, Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of formula I. The concentration of test compound corresponds to a rate of application of up to 100 g a.i. per hectare. The growth of the grasses is evaluated 21 days after application.

The compounds of formula I effect a reduction in new growth in the range of 10-30% in comparison with untreated controls.

What is claimed is:

1. An N-(3,4-dihydro-2,2-dioxo-1,2-benzoxathiin-8-ylsulfonyl)-N'-triazinylurea of formula I $$\text{(I)}$$

[Structure: benzene ring fused with SO$_2$-O-CHR$^3$ forming benzoxathiin; R$^1$ and R$^2$ substituents on ring; ring carries —SO$_2$—NH—C(=W)—N(R$^4$)—A]

wherein
R$^1$ is hydrogen, halogen, nitro, C$_1$-C$_4$alkyl, C$_1$-C$_4$haloalkyl, C$_1$-C$_4$alkoxy, C$_1$-C$_4$haloalkoxy, C$_1$-C$_4$alkoxycarbonyl, C$_1$-C$_4$alkylthio, C$_1$-C$_4$alkylsulfinyl, C$_1$-C$_4$alkylsulfonyl or C$_2$-C$_5$alkoxyalkoxy,
R$^2$ and R$^3$ are each independently of the other hydrogen or C$_1$-C$_4$alkyl,
R$^4$ is hydrogen, methyl or ethyl, W is oxygen or sulfur, and
A is a radical

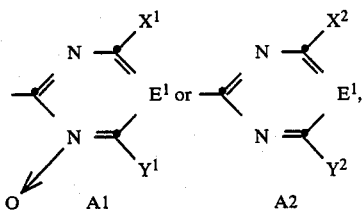

in which formulae
$X^1$, $X^2$ and $Y^1$ are each independently halogen, $C_1$–$C_4$haloalkoxy, $C_1$–$C_4$haloalkyl, $C_1$–$C_4$alkoxy, $C_1$–$C_4$alkyl, dimethylamino, methylamino, ethylamino, amino or $C_2$–$C_4$alkoxyalkyl,
$E^1$ is nitrogen,
$Y^2$ is cyclopropyl, dimethoxymethyl, diethoxymethyl,

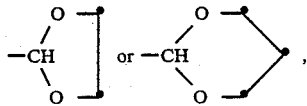

or salt thereof; with the proviso that $R^3$ is $C_1$–$C_4$alkyl if A is A2.

2. A compound according to claim 1, wherein $R^1$ and $R^2$ are hydrogen and $R^3$ is methyl.

3. A compound according to claim 1, wherein W is oxygen.

4. A compound according to claim 1, wherein $R^4$ is hydrogen.

5. A compound according to claim 1, wherein W is oxygen and $R^4$ is hydrogen.

6. A compound according to claim 1, wherein W is oxygen, $R^4$ is hydrogen and A is the group A1, in which $X^1$ is $C_1$–$C_4$alkyl.

7. A compound according to claim 1, wherein W is oxygen, $R^4$ is hydrogen and A is the group A2, in which $Y^2$ is cyclopropyl.

8. N-(3,4-Dihydro-3-methyl-2,2-dioxo-1,2-benzoxathiin-8-yl-sulfonyl)-N'-(4,6-dimethyl-1-oxo-1,3,5-triazin-2-yl)urea according to claim 1.

9. N-(3,4-dihydro-3-methyl-2,2-dioxo-1,2-benzoxathiin-8-ylsulfonyl)-N'-(4-cyclopropyl-6-methoxy-1,3,5-triazin-2-yl)-urea according to claim 1.

10. A herbicidal and plant growth inhibiting composition which contains, as active ingredient, an effective amount of a substituted sulfonylurea of formula I according to claim 1, together with a carrier or other adjuvant.

11. A method of controlling undesired plant growth, which method comprises applying to the plants or to the locus thereof an effective amount of a compound of formula I according to claim 1, or of a composition containing such a compound.

12. A method of inhibiting plant growth, which method comprises applying to the plants or to the locus thereof an effective amount of a compound of formula I according to claim 1, or of a composition containing such a compound.

13. A method of influencing plant growth for increasing yield, which method comprises applying to the plants or to the locus thereof an effective amount of a compound of formula I according to claim 1, or of a composition containing such a compound.

14. A method according to claim 11 of selectively controlling weeds pre- or postemergence in crops of useful plants.

15. A method according to claim 12 of suppressing plant growth beyond the 2-leaf stage, which method comprises applying the active ingredient preemergence.

* * * * *